(12) United States Patent
Hume et al.

(10) Patent No.: US 6,481,360 B2
(45) Date of Patent: Nov. 19, 2002

(54) ULTRA FINE FLY ASH AND A SYSTEM FOR COLLECTING THE SAME

(75) Inventors: John D. Hume, New Albany; R. F. Ridgeway, Reynoldsburg; J. F. Mainieri, Granville, all of OH (US)

(73) Assignee: American Electric Power Service Corporation, Columbus, OH (US)

( * ) Notice: Subject to any disclaimer, the term of this patent is extended or adjusted under 35 U.S.C. 154(b) by 0 days.

(21) Appl. No.: 09/779,250

(22) Filed: Feb. 8, 2001

(65) Prior Publication Data

US 2001/0015159 A1 Aug. 23, 2001

Related U.S. Application Data

(62) Division of application No. 09/388,322, filed on Sep. 1, 1999, now Pat. No. 6,216,612.

(51) Int. Cl.⁷ .............................. F23J 1/02; B01D 45/00
(52) U.S. Cl. .............................. 110/165 R; 110/165 A; 110/169; 55/343
(58) Field of Search .................. 110/165 A, 165 R, 110/166, 167, 168, 169, 216, 344, 345; 209/12.1, 30, 31, 21, 19; 55/DIG. 30, 385.1, 337, 315, 343, 334, 349, 321, 323

(56) References Cited

U.S. PATENT DOCUMENTS

4,244,717 A * 1/1981 Butcher ...................... 55/364

* cited by examiner

Primary Examiner—Ira S. Lazarus
Assistant Examiner—K. B. Rinehart
(74) Attorney, Agent, or Firm—Sand & Sebolt

(57) ABSTRACT

A system for collecting ultra fine fly ash from a dry fly ash removal system includes providing a bagfilter transport conduit for each bagfilter of the system. A vacuum shutoff valve is positioned in each bagfilter transport conduit The bagfilter transport conduit is selectively connected to an educator that is, in turn, selectively connected to a blower. The blower creates a vacuum flow in the transport conduit that draws the ultra fine fly ash from the bagfilter and deposits the ultra fine fly ash in a collection bin. This system allows a dry fly ash removal system to segregate fly ash by size and separately collect the ultra fine fly ash from the larger fly ash particles. The ultra fine fly ash has been found to be commercially valuable as a concrete admixture filler in various applications.

28 Claims, 6 Drawing Sheets

ULTRA FINE FLY ASH AND A SYSTEM FOR COLLECTING THE SAME

CROSS REFERENCE TO RELATED APPLICATION

This application is a division of copending U.S. patent application Ser. No. 09/388,322 filed Sep. 1, 1999 now U.S. Pat. No. 6,216,612.

BACKGROUND OF THE INVENTION

1. Technical Field

This invention generally relates to the control of emissions from combustion processes such as coal-fired processes or other combustion processes that produce large quantities of solid fly ash particles. More particularly, the present invention relates to a system and method for segregating the separated fly ash particles based on particle size and collecting the segregated particles into individual storage containers. Specifically, the present invention relates to a separation system that allows ultra fine fly ash to be separately collected from a dry fly ash removal system by providing a dedicated removal system for removing fly ash particles only from the last separation device of the system.

2. Background Information

The combustion of coal and other similar fuels produces molten inorganic matter that is carried away in the exhaust gas stream as the fuel burns. The molten inorganic matter cools as the exhaust stream flows away from the combustion and coalesces into spherical or ellipsoidal ceramic particles in the general range of 0.01 to 500 microns in diameter. These combustion by-product particles are known in the art as fly ash.

Fly ash must be removed from combustion exhaust streams before the streams are exhausted to the atmosphere because of environmental concerns. Numerous methods and systems for removing fly ash are known in the art that effectively remove the fly ash from an exhaust stream. One problem common to all of these methods and systems is the cost of disposing of the collected fly ash. Although some of the fly ash may be sold for various commercial purposes such as for fillers, most fly ash must be landfilled at the expense of the company creating the fly ash. It is thus desired in the art to increase the quantity of commercially-valuable fly ash and consequently decrease the amount of fly ash that must be landfilled.

One known system that separates fly ash from a combustion exhaust stream is an electrostatic precipitator 12 depicted in FIGS. 1 and 2. Other systems 12 that will function with the concepts of the present invention are separation systems such as bag filters, cyclones, and others know in the art. Separation system 12 may be positioned as the final cleaning step for an exhaust stream from a coal-fired power production process. For instance, system 12 may be used in a power production process where coal is burned to create heat that produces steam to run generators. The burning coal creates an exhaust stream containing fly ash that must be substantially removed from the stream according to federal regulations. System 8 is a Fly Ash Removal System (FARS) which transports ash from the hoppers of the separation device 12. FARS 8 transports the fly ash pneumatically to a storage facility (i.e. silo, pond, etc). The conveying air can be either a pressure or vacuum system. In the example of system 8 depicted in FIG. 1, the ash enters system 8 directly from an inlet conduit 10 that receives ash from electrostatic precipitator 12 positioned above conduit 10 and receives its transport air from air intake 11.

Inlet 10 feeds a primary supply line 14 that is in communication with a plurality of separation units 16. In this embodiment of system 8, four separation units 16 are connected to primary supply line 14 in parallel such that each unit 16 receives substantially equal amounts of the fly ash-laden transport air. In other embodiments, a separate, individual precipitator may be used to deliver fly ash-laden transport air to each unit 16 without departing from the concepts of the present invention. Additional or fewer units 16 may be provided based on flow rate, need, and desired redundancies. Further systems 8 for one or more power producers may also utilize a silo 40 common to all systems 8.

Each separation unit 16 includes a feed line 18 that connects primary supply line 14 to a coarse separator 20. There is a shut off valve between supply line 14 and feed line 18. In this example, each coarse separator 20 includes a primary separator 22 connected to a secondary separator 24. In the preferred embodiment of the present invention, each separator 22 and 24 is cyclone. Feed line 18 is connected to the inlet of primary separator 22 such that the fly ash-laden transport air is drawn into the separation chamber of primary separator 22. The transport air exits primary separator 22 through an outlet 26 after at least a portion of the fly ash falls out of the transport air stream into a primary receiver 28. The separated fly ash exists through a first gate 30 that selectively opens and closes the outlet 32 to primary receiver 28. A storage hopper 34 is disposed below outlet 32 to collect the fly ash. The outlet 36 of storage hopper 34 is selectively opened and closed by a hopper gate 38. Storage hopper 34 is positioned above a collection silo or storage container 40 that gathers fly ash from each separation unit 16. A pressure equalization system 35 is provided to regulate the pressure in the system.

Outlet 26 of primary separator 22 is connected directly to the inlet 42 of secondary separator 24. Second cyclone 24 has an outlet 44 through which the transport air is drawn and a secondary receiver 46 where the fly ash removed by secondary separator 24 is temporarily collected. The outlet 48 of secondary receiver 46 is selectively opened and closed by a secondary gate 50 that selectively opens secondary receiver 46 to storage hopper 34.

Outlet 44 is connected to the inlet 52 of a tertiary separator 54. Each tertiary separator 54 is preferably a bagfilter in system 8. Other separators such as ceramic filters or other high efficiency separating devices known in the industry may also be used as the tertiary separator. Each bagfilter 54 is designed and configured to remove the smallest particles of fly ash from the transport air before it enters a vacuum pump 58. Bagfilters 54 thus function as a final cleaning step for the transport air. A bagfilter transfer conduit 56 connects outlet 44 of each coarse separator 20 to inlet 52 of bagfilter 54. The transport air flow is pulled through system 8 by vacuum pump 58.

As is known in the art, bagfilter 54 may often use a collection of fabric filters, similar to common household vacuum cleaners, but at a much larger scale, to entrap air-borne particulate matter onto a filter surface, allowing the largely particulate-free air to continue through the filter surface. During operation of bagfilter 54, particulate matter builds up on the surface of the filter. This buildup is commonly known as the bag's cake. Cakes are frequently allowed to build up to thicknesses of approximately 0.25 inch or somewhat more between intervals of cleaning. Bags in operational bagfilters are cleaned of cake buildup at periodic intervals that are determined by variables of operation and engineering design. The cleaning process often involves blowing air backwards through the bag filters, shaking the bags, or banging the tops of the bags, all of which cause a substantial portion of the filter cake to drop off the bags.

In system 8, the bags of each bagfilter 54 are cleaned by knocking the cakes off of the bags and dumping the cake material into an open hopper 60. First gate 61 selectively opens and closes into a transfer hopper 62. Transfer hopper 62 is selectively opened and closed by a second gate 64 that controls access to silo 40. The fly ash separated by bagfilter 54 is moved into hopper 62 and dumped into silo 40. A pressure equalization system 63 is provided to control the pressure in the system because the bag filter is under vacuum and the silo is not. As such, the fly ash collected in bagfilters 54 is mixed with the fly ash collected in coarse separator 20 and is commonly disposed. Silo 40 is emptied through a rotary conditioning drum 66 and into a vehicle 68 that transports the fly ash to another location.

It has been discovered as part of the present invention that the fly ash collected in bagfilters 54 is commercially valuable and that it is desirable to separately collect this fly ash. It has been found that the fly ash collected in bagfilters 54 comprises a plurality of particles with 90% of the particles having a diameter of less than 10 microns. It is known in the art that fly ash particles having diameters predominantly smaller than 25 microns are known as fine fly ash. U.S. Pat. No. 4,294,750 discloses the benefits of fine fly ash particles. The present invention refers to fly ash particles that are predominantly smaller than 10 microns in diameter as ultra fine fly ash. It is thus desired in the art to provide a system for collecting the fly ash from bagfilters 54 that does not combine the fly ash from bagfilters 54 with any fly ash from separators 22 and 24.

SUMMARY OF THE INVENTION

In view of the foregoing, it is an objective of the present invention to provide a method for separating ultra fine fly ash from larger fly ash particles in a dry fly ash removal system and collecting the ultra fine fly ash particles for later use.

Another objective of the present invention is to provide a system that allows ultra fine fly ash particles to be collected separately from larger fly ash particles in a dry fly ash removal system.

Another objective of the present invention is to provide an ultra fine fly ash material having characteristics that are desired in fillers for various applications.

Another objective of the present invention is to provide a system and method for separating fly ash that results in less fly ash being landfilled.

Another objective of the present invention is to provide a system and method for economically collecting ultra fine fly ash.

Another objective of the present invention is to provide a system, as above, that may be retrofit into existing dry fly ash removal systems.

Another objective of the present invention is to provide a system, as above, that pneumatically transfers the separated ultra fine fly ash to a dedicated storage container.

Another objective of the present invention is to provide a system, as above, that selectively collects the ultra fine fly ash so that the ultra fine fly ash only resides in the storage container a short time prior to off-site transfer.

Another objective of the present invention is to provide an effective, safe, inexpensive and efficient device that achieves all the enumerated objectives, provides for eliminating difficulties encountered with prior devices, and solves problems and obtains new results in the art.

These and other objectives and advantages of the present invention are achieved by a method for collecting ultra fine fly ash from a dry fly ash removal system having an inlet that directs a fly ash-laden transport air stream into a coarse separator where a portion of the fly ash is removed from the transport air stream and a bagfilter in fluid communication with the outlet of the coarse separator where the ultra fine fly ash is removed from the transport air stream; the method including the steps of: (a) providing a transport conduit connected to the bagfilter; (b) removing the ultra fine fly ash from the bagfilter; and (c) storing the ultra fine fly ash removed from the bagfilter separate from the fly ash removed by the coarse separator.

Other objectives and advantages of the invention are achieved by a system for collecting particulate material, including an inlet; a separator in fluid communication with the inlet; a bagfilter in fluid communication with the separator; a collection silo in selective communication with the separator and the bagfilter; a gate configured to selectively block the fluid communication between the bagfilter and the collection silo; and a transport conduit in fluid communication with the bagfilter between the gate and the bagfilter.

Further objectives and advantages of the present invention are achieved by particulate material, useful as a filler, composed of particles at least about 90 percent of which (volume basis) have a particle size less than about 10 microns.

BRIEF DESCRIPTION OF THE DRAWINGS

The preferred embodiments of the invention, illustrative of the best mode in which applicant contemplated applying the principles of the invention, are set forth in the following description and are shown in the drawings and are particularly and distinctly pointed out and set forth in the appended claims.

Similar numbers refer to similar parts throughout the drawings.

DESCRIPTION OF THE PREFERRED EMBODIMENT

Figure 1:
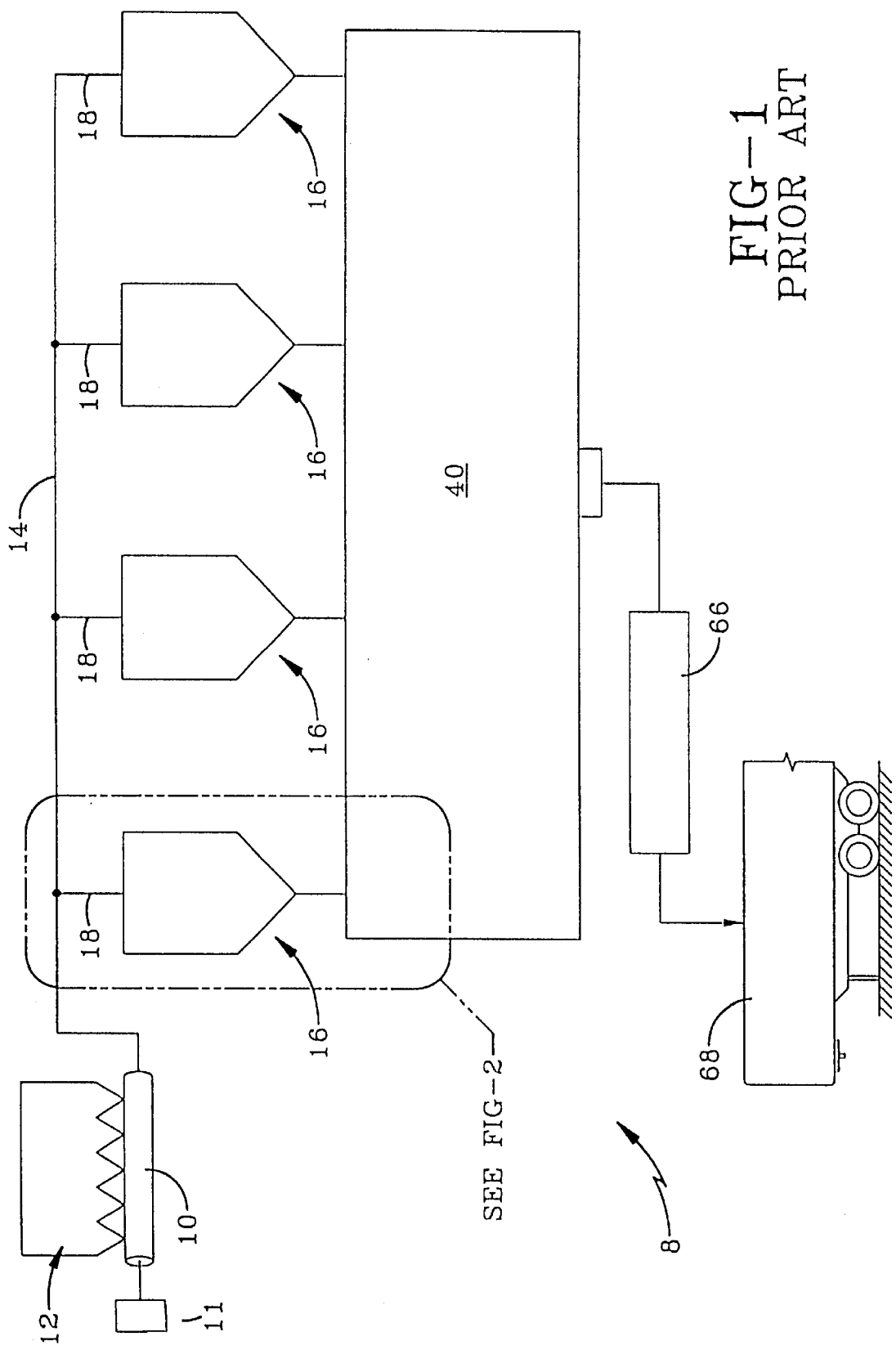
FIG. 1 is a schematic view of a prior art dry fly ash removal system.
Figure 2:
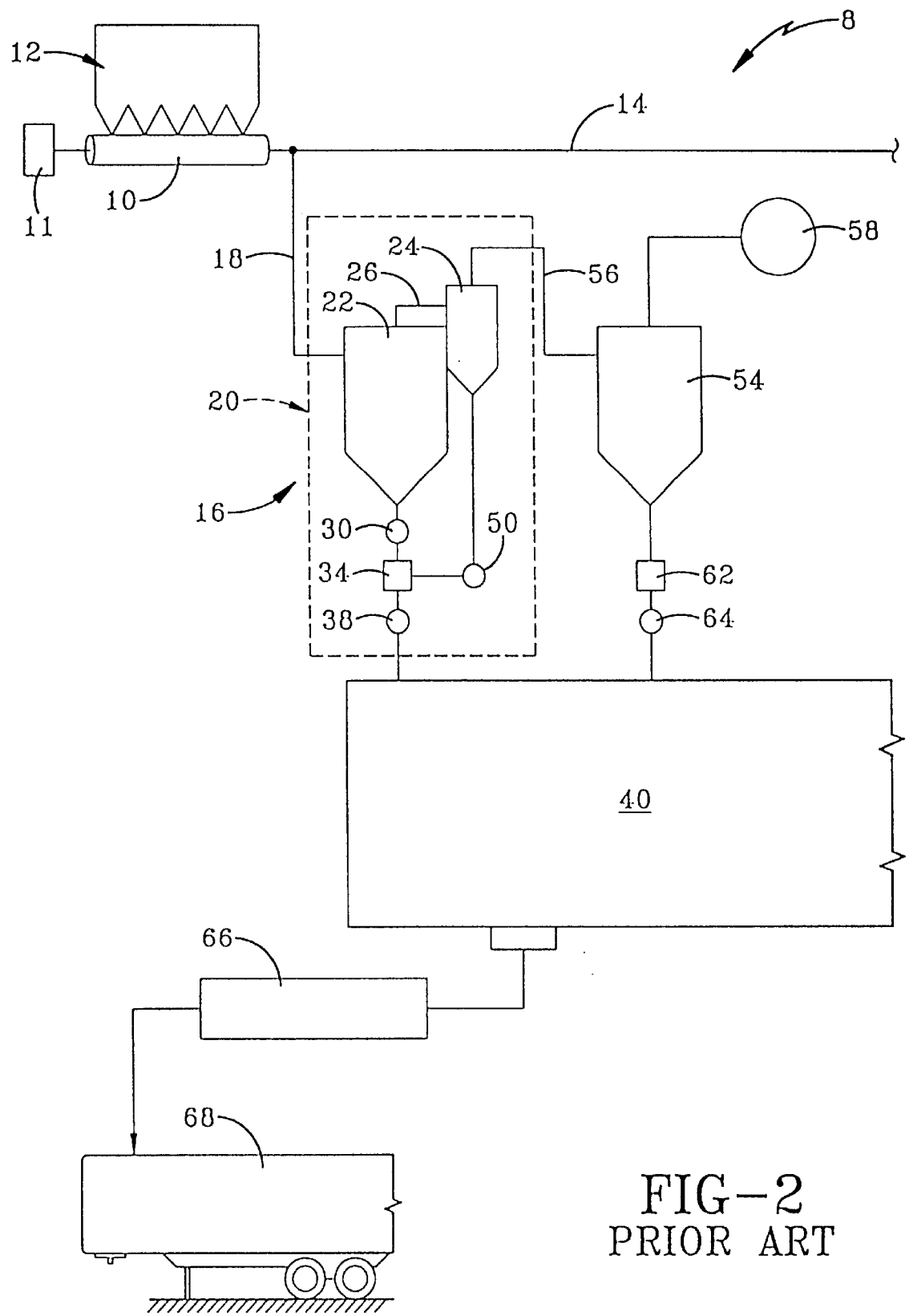
FIG. 2 is a schematic view of the portion of the dry fine fly ash removal system encircled in FIG. 1.
Figure 3:
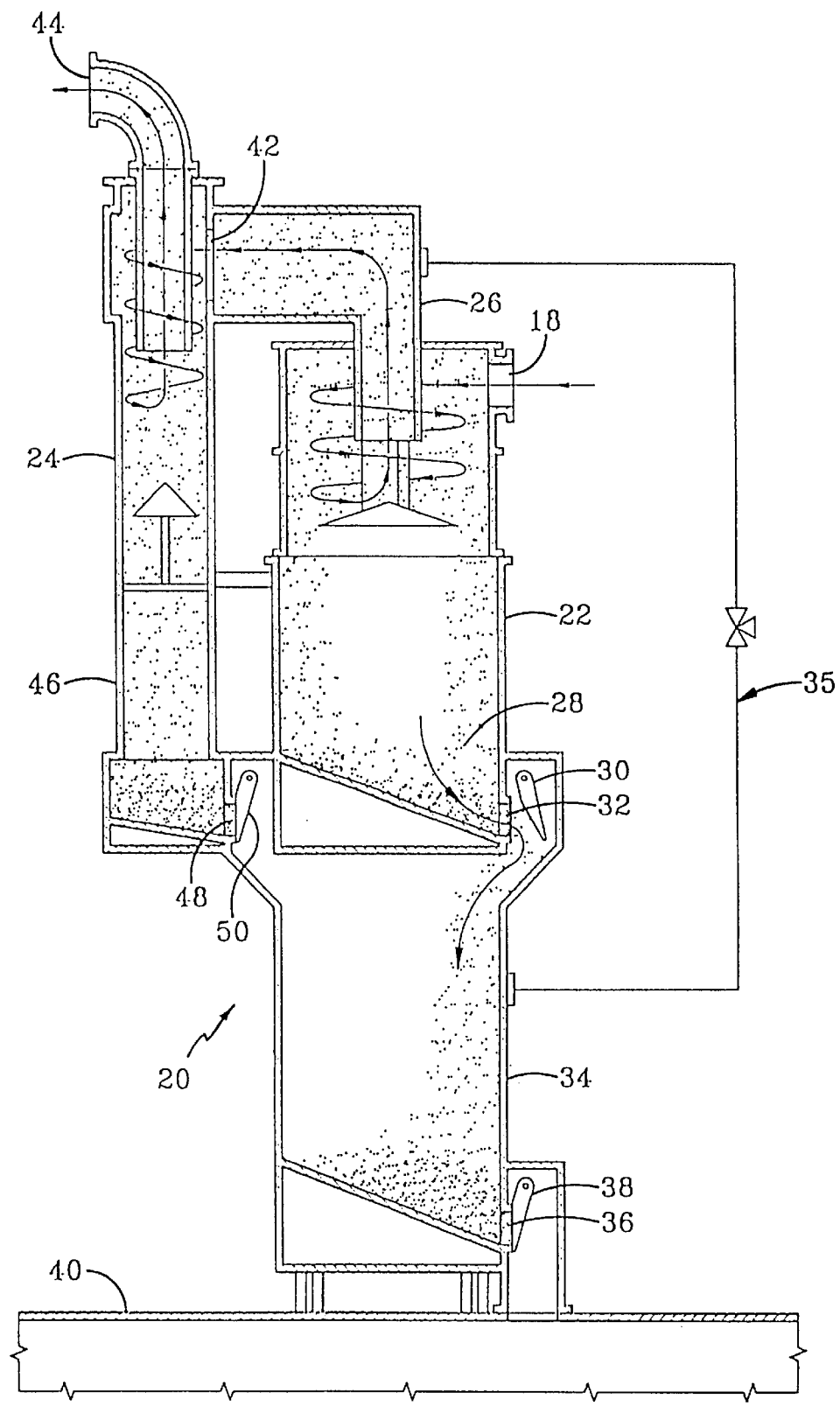
FIG. 3 is a diagrammatic sectional view of the first and second cyclones of the prior art dry fly ash removal system.
Figure 4:
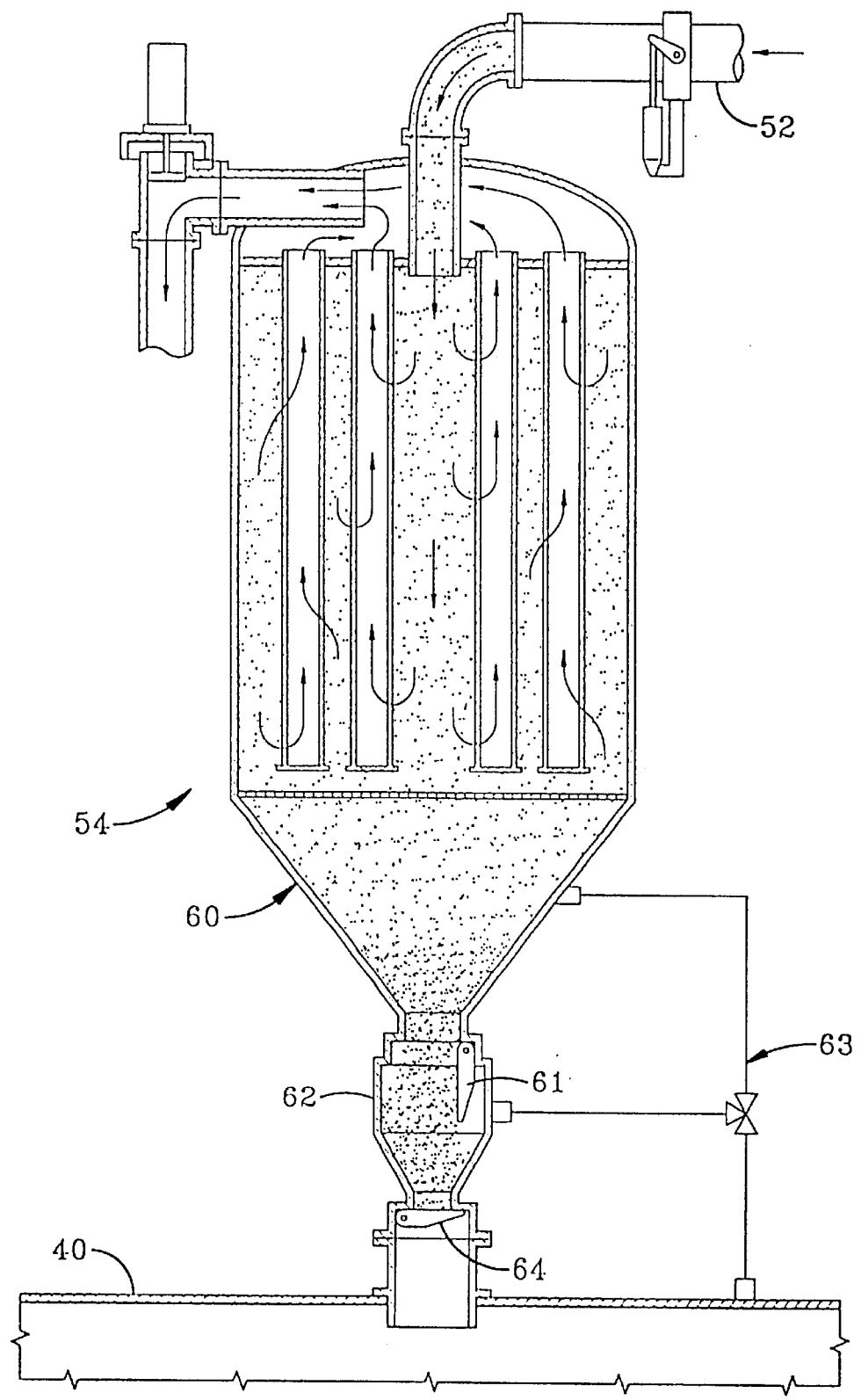
FIG. 4 is a diagrammatic sectional view of one bagfilter of the prior art dry fly ash removal system.
Figure 5:
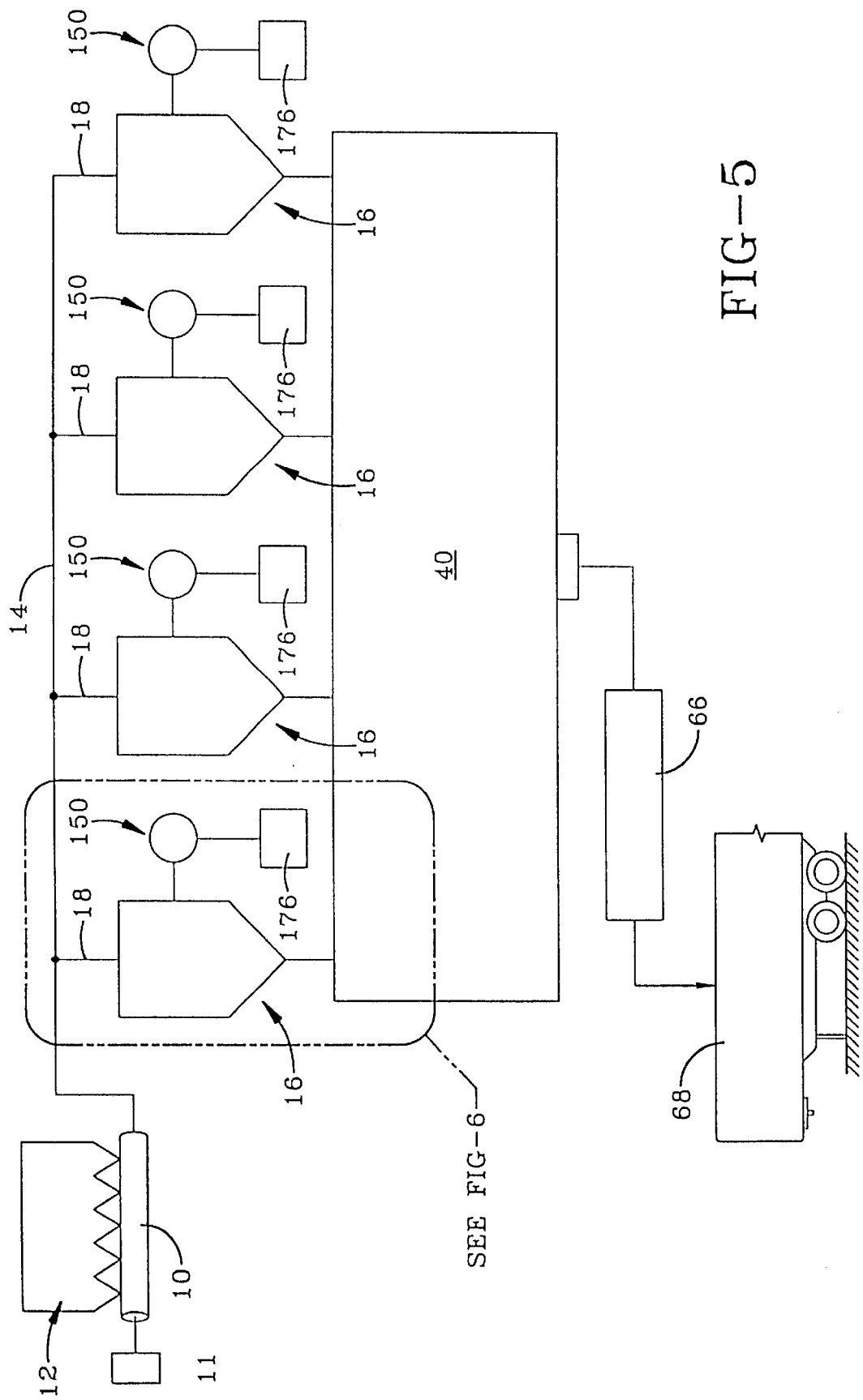
FIG. 5 is a schematic view of the ultra fine fly ash removal system of the present invention.
Figure 6:
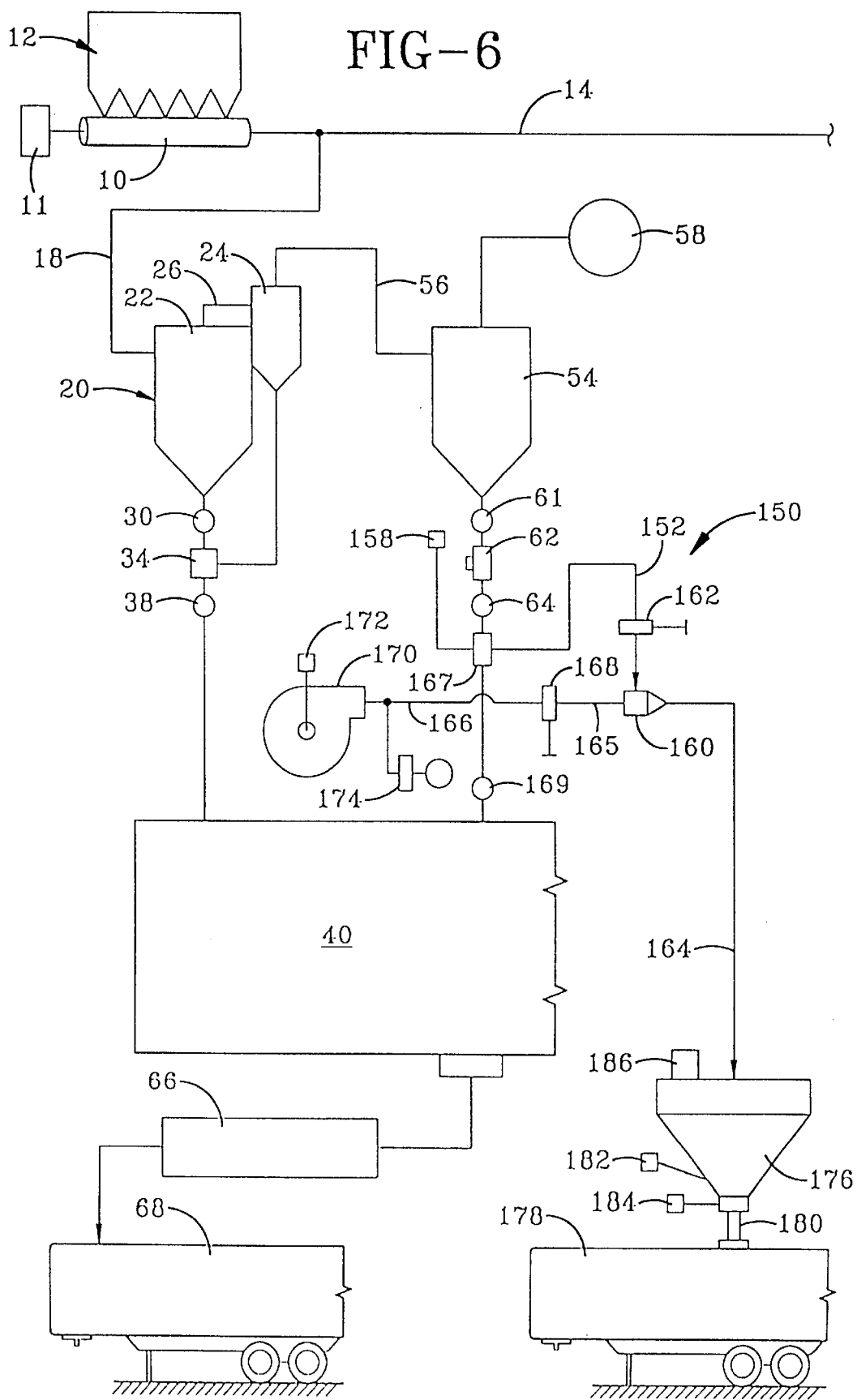
FIG. 6 is schematic view of the encircled portion of the ultra fine fly ash removal system of FIG. 5.

The ultra fine fly ash removal system of the present invention is indicated generally by the numeral 150 in FIGS. 5 and 6. System 150 may be retrofit into system 8 and thus includes substantially all of the elements of system 8 and the numbers introduced above are used in FIGS. 5 and 6 to indicate the elements of system 8. System 150 allows the fly ash particles collected in bagfilters 54 to be separately collected from the fly ash particles collected in separators 20. Such segregated separation is desired because the ultra fine fly ash particles collected in bagfilters 54 have been found to be commercially valuable. It has been found that the fly ash particles collected in bagfilters 54 are predominantly finer than 10 microns in diameter. In accordance with one of the objectives of the present invention, the ultra fine fly ash particles collected in bagfilters 54 are commercially useful as additives and fillers for such applications as concrete, paint, sealant, polymers, etc. System 150 of the present invention allows these ultra fine fly ash particles to be easily collected from dry fly ash removal system 8 at selected times when such collection is desired.

System 150 is created by modifying system 8 by first providing a silo shutoff valve 169 and by providing an ultra fine fly ash transport conduit 152 that is in communication with a discharge chute 167 positioned below each transfer hopper 62. The present invention also contemplates that transport conduit 152 may be connected directly to bagfilter 54 instead of the connection through hopper 62. Conduit 152 may be connected to discharge chute 167 by an appropriate connector. An air inlet check valve 158 allows air to flow into discharge chute 167 from the surrounding atmosphere so that an ultra fine fly ash removal flow may be created in discharge chute 167 as will be described in more detail below.

Each bagfilter transport conduit 152 is in selective fluid communication with an educator 160. The selective fluid communication is provided by a vacuum shutoff valve 162 disposed between educator 160 and discharge chute 167. Each educator 160 is in communication with air supply line 165 that may be in selective fluid communication with an air supply header 166. The selective communication between each air supply line 165 and air supply header 166 may be provided by an air supply shutoff valve 168 positioned between educator 160 and air supply header 166.

Air supply header 166 is in fluid communication with a transport air blower 170 that is positioned at the upstream end of the air supply header 166. Transport air blower 170 includes an inlet filter 172 and an automatic transport air dump valve 174.

Eductor 160 is also in communication with an ultra fine ash transport line 164. The downstream end of each ultra fine ash transport line 164 is in communication with an ultra fine fly ash storage silo 176. Storage silo 176 is selectively connected to a transport vehicle 178 by a suitable connection 180 such as a flexible chute. Storage silo 176 also includes a compressed air flow inducer 182 and a discharge valve 184. Storage silo 176 further includes an outlet filter 186.

FIG. 5 depicts each ultra fine ash storage silo 176 as a separate silo for each separation unit 16. It is also contemplated by the present invention that a single silo 176 may be used with each ultra fine ash transport line 164 extending from eductor 160 to the single storage silo 176. In this situation, air supply header 166 supplies pressurized air to each air supply line 165 through a plurality of air supply shut off valves 168.

In the preferred embodiment of the present invention, each air supply line 165 and each ultra fine ash transport line 164 is fabricated from two inch pipe with air supply header 166 being fabricated from four inch pipe. Transport blower 170 may be a Holmes transport blower. Storage silo 176 may be sized to hold approximately 2,500 cubic feet of ultra fine fly ash with transport vehicle 178 being a dry bulk tank truck. Valves 162, 168, and 184 may be manually operated or automatically operated valves of any of a variety of suitable valves known in the art.

In normal operation of the dry fly ash removal system, vacuum shutoff valves 162 are closed and silo shutoff gates 169 are open with system 8 operating to remove fly ash from the transport air. The fly ash-laden transport air stream is directed into separator 20 where the larger particles of fly ash are removed and then directed into bagfilters 54 where the ultra fine fly ash is removed and discharged via transfer hopper 62 to silo 40.

To collect the ultra fine fly ash, the user opens each transport air shutoff valve 168 to provide fluid communication between educator 160 and blower 170. Blower 170 is then operated and let run for a few minutes to warm the piping system and drive off any condensation. The ultra fine fly ash from each bagfilter 54 may then be collected by closing silo shutoff gate 169, thus allowing ultra fine fly ash to collect in the discharge chute 167, and opening its vacuum shutoff valve 162 to create the ultra fine fly ash removal flow in the form of a vacuum flow through its transport conduit 152. The removal flow draws the ultra fine fly ash from discharge chute 167 into transport air line 164 where it is transported into storage silo 176. Transfer hopper 62 feeds discharge chute 167 while the process continues.

In other embodiments of the present invention the ultra fine fly ash may be removed from the bagfilter by positioning the bagfilter between its transport conduit 152 and a blower that creates the ultra fine fly ash removal flow through transport conduit 152. System 150 will also function with gate 61 closed prior to evacuating hopper 62.

In some embodiments of the present invention, each bagfilter 54 may be exposed to an ultra fine fly ash removal flow simultaneously. In other embodiments, bagfilters 54 are sequentially exposed to the ultra fine fly ash removal flow such that ultra fine fly ash is only removed from one bagfilter at a time.

During the removal process, the operator monitors the height of the material in storage silo 176. In one example, the expected collection rate for a system 150 having four bagfilters 54 is approximately 1,500 pounds per hour per bagfilter, or three tons per hour for collecting all four bagfilters 54. The expected collection time for a 23 ton dry bulk truck is thus approximately seven to eight hours.

In one example taken from the baghouse at the Sporn plant located in New Haven, W.Va., which primarily burns low sulfur, eastern bituminous coal, the ultra fine fly ash collected from the baghouse comprised particles of which 90% (volume basis) had a diameter of less than about 10 microns. About 50% (volume basis) of the ultra fine fly ash particles had a diameter of less than about 3.7 microns. The particles had a specific gravity of 2.31, a moisture content of 0.18%, a loss on ignition of 5.44%. The autoclave expansion (per ASTM C-151) of a composite cement paste made with 400 g of Portland cement and 100 g ultra fine fly ash is within the specification and typically results in a negative valve (e.g. −0.05%). The pozzolonic activity of this sample of ultra fine fly ash measured in accordance with ASTM C-311 (with the water requirement being 100% of the control) is better than most class F ashes. Replacing 25% of the Portland cement in comparison with a 100% Portland cement control resulted in a compressive strength of 92% of the control at 7 days which is well within the requirements of the ASTM C-618.

The analysis of the ultra fine fly ash resulted in 53% silica ($SiO_2$); 27.6% aluminum oxide ($Al_2O_3$); 7.9% iron oxide ($Fe_2O_3$); 1.4% titanium oxide ($TiO_2$); 1% calcium oxide (CaO); 0.7% magnesium oxide (MgO); 0.3% sodium oxide ($Na_2O$); 2.2% potassium oxide ($K_2O$); 0.6% sulfur trioxide ($SO_3$); 0.3% phosphorous pentoxide ($P_2O_5$); 0.1% barium oxide (BaO); less than 0.1% manganese oxide ($Mn_2O_3$); less than 0.1% strontium oxide (SrO); 4.5% total carbon, and 0.4% net ignition loss (+)/gain(−). The tests also revealed a loss on ignition (LOI) at 750° Celsius of 5.3; a pH at 25° Celsius, s.u. (1% slurry) of 4.9; and a specific conductance at 25° Celsius, $\mu$mh (1% slurry) of 139.

In general, the ultra fine fly ash particles have a specific gravity in the range of 2.1 to 2.4 and a hegman fineness in the range of 5 to 8. The pH falls in the range of 4.5 to 7 and the bulk density falls in the general range of 40 to 60 pcf. The loss on ignition is also less than 8 percent.

Accordingly, the ultra fine dry fly ash collection system is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness, and understanding; but no unnecessary limitations are to be implied therefrom beyond the requirement of the prior art, because such terms are used for descriptive purposes and are intended to be broadly construed.

Moreover, the description and illustration of the invention is by way of example, and the scope of the invention is not limited to the exact details shown or described.

Having now described the features, discoveries, and principles of the invention, the manner in which the ultra fine dry fly ash collection system is constructed and used, the characteristics of the construction, and the advantageous new and useful results obtained; the new and useful structures, devices, elements, arrangements, parts, and combinations are set forth in the appended claims.

What is claimed is:

1. A system for collecting particulate material, comprising:
   an inlet;
   a separator in fluid communication with the inlet;
   a bagfilter in fluid communication with the separator;
   a collection silo in selective communication with the separator and the bagfilter;
   a gate configured to selectively block the fluid communication between the bag filter and the collection silo; and
   an eductor in selective fluid communication with the bagfilter; and
   a vacuum shutoff valve selectively blocking the fluid communication between the bagfilter and the eductor.

2. The system of claim 1, further comprising an air inlet check valve disposed between the gate and the bagfilter.

3. The system of claim 1, further comprising a blower in selective fluid communication with the eductor.

4. The system of claim 3, further comprising an air supply shutoff valve providing the selective fluid communication between the blower and the eductor.

5. The system of claim 3, further comprising a collection bin and a transport air line in fluid communication with the eductor and the collection bin.

6. The system of claim 5, further comprising an outlet filter connected to the collection bin.

7. The system of claim 6, further comprising a compressed air inducer connected to the collection bin.

8. The system of claim 7, further comprising a discharge valve connected to the collection bin.

9. The system of claim 1, further comprising a second separator in fluid communication with the inlet;
   a second bagfilter in fluid communication with the second separator;
   a second gate selectively blocking the fluid communication between the second bagfilter and the collection silo; and
   a second transport conduit in fluid communication with the second bagfilter.

10. The system of claim 9, further comprising a third separator in fluid communication with the inlet;
    a third bagfilter in fluid communication with the third separator;
    a third gate selectively blocking the fluid communication between the third bagfilter and the collection silo; and
    a third transport conduit in fluid communication with the third bagfilter.

11. The system of claim 10, further comprising a fourth separator in fluid communication with the inlet;
    a fourth bagfilter in fluid communication with the fourth separator;
    a fourth gate selectively blocking the fluid communication between the fourth bagfilter and the collection silo; and
    a fourth transport conduit in fluid communication with the fourth bagfilter.

12. In a dry fly ash removal system having an inlet; a separator in fluid communication with the inlet; and a bagfilter in fluid communication with the separator, and a collection silo in selective communication with the separator and the bagfilter; the improvement comprising:
    a bagfilter transport conduit commented to the bagfilter such that fly ash may be removed from the bagfilter and collected and stored separately from the fly ash collected in the separator;
    an eductor in selective fluid communication with the transport conduit; and
    a vacuum shutoff valve disposed between the eductor and the bagfilter; the vacuum shutoff valve configured to provide the selective fluid communication between the eductor and the bagfilter discharge chute.

13. the improvement of claim 12, further comprising;
    a storage silo;
    a transport air line extending between the eductor adnt eh storage silo;
    a blower;
    an air supply header in fluid communication with the blower;
    an air supply line in fluid communication with the eductor; and
    an air supply shutoff valve providing selective fluid communication between the air supply header and the air supply line.

14. The improvement of claim 13, wherein the blower has an inlet and a filter in fluid communication with the inlet.

15. The improvement of claim 13, further comprising an outlet filter connected to the collection bin.

16. The improvement of claim 15, further comprising a source of compressed air in fluid communication with the collection bin.

17. The improvement of claim 16, further comprising a transport vehicle selectively connected to the collection bin.

18. The improvement of claim 17, further comprising a flexible chute connecting the collection bin to the transport vehicle.

19. The improvement of claim 12, further comprising an air inlet check valve in fluid communication with the bagfilter transport conduit.

20. A system for collecting particulate material, comprising;
   an inlet;
   a separator in fluid communication with the inlet;
   a bagfilter in fluid communication with the separator;
   a collection silo in selective communication with the separator and the bagfilter;
   a gate configured to selectively block the fluid communication between the bagfilter and the collection silo;
   a transport conduit in fluid communication with bagfilter between the gate and the bagfilter;
   an eductor in selective fluid communication with the bagfilter;
   a blower in selective fluid communication with the eductor; and
   an air supply shutoff valve providing the selective fluid communication between the blower and the eductor.

21. In a dry fly ash removal system having an inlet; a separator in fluid communication with the inlet; and a bagfilter in fluid communication with the separator, and a collection silo in selective communication with the separator and the bagfilter; the improvement comprising:
   a bagfilter transport conduit connected to the bagfilter such that fly ash may be removed from the bagfilter and collected and stored separately from the fly ash collected in the separator; and
   an air inlet check valve in fluid communication with the bagfilter transport conduit.

22. The system of claim 20, further comprising a collection bin and a transport air line in fluid communication with the eductor and the collection bin.

23. The system of claim 22, further comprising an outlet filter connected to the collection bin.

24. The system of claim 23, further comprising a compressed air inducer connected to the collection bin.

25. The system of claim 24, further comprising a discharge valve connected to the collection bin.

26. The system of claim 20, further comprising a second separator in fluid communication with the inlet;
   a second bagfilter in fluid communication with the second separator;
   a second gate selectively blocking the fluid communication between the second bagfilter and the collection silo; and
   a second transport conduit in fluid communication with the second bagfilter.

27. The system of claim 26, further comprising a third separator in fluid communication with the inlet;
   a third bagfilter in fluid communication with the third separator;
   a third gate selectively blocking the fluid communication between the third bagfilter and the collection silo; and
   a third transport conduit in fluid communication with the third bagfilter.

28. The system of claim 27, further comprising a fourth separator in fluid communication with the inlet;
   a fourth bagfilter in fluid communication with the fourth separator;
   a fourth gate selectively blocking the fluid communication between the fourth bagfilter and the collection silo; and
   a fourth transport conduit in fluid communication with the fourth bagfilter.

* * * * *